United States Patent
Borgaonkar et al.

(10) Patent No.: US 7,881,808 B2
(45) Date of Patent: Feb. 1, 2011

(54) CONDUCTIVE POLYMERIC COATING WITH OPTIONAL BIOBENEFICIAL TOPCOAT FOR A MEDICAL LEAD

(75) Inventors: Harshad Borgaonkar, Blaine, MN (US); Piotr Waszczuk, St. Paul, MN (US); Daniel J. Cooke, Roseville, MN (US); Xiangchun Jiang, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 739 days.

(21) Appl. No.: 11/277,858

(22) Filed: Mar. 29, 2006

(65) Prior Publication Data

US 2007/0239245 A1 Oct. 11, 2007

(51) Int. Cl.
*A61N 1/00* (2006.01)
(52) U.S. Cl. ...................................... 607/122
(58) Field of Classification Search ............... 427/2.1, 427/2.11, 2.12; 600/115–122
See application file for complete search history.

(56) References Cited

U.S. PATENT DOCUMENTS

| | | | |
|---|---|---|---|
| 4,928,689 A | 5/1990 | Hauser | |
| 5,103,837 A | 4/1992 | Weidlich et al. | |
| 5,282,844 A | 2/1994 | Stokes et al. | |
| 5,324,324 A * | 6/1994 | Vachon et al. | 607/120 |
| 5,385,579 A * | 1/1995 | Helland | 607/130 |
| 5,766,527 A | 6/1998 | Schildgen et al. | |
| 5,837,313 A | 11/1998 | Ding et al. | |
| 5,853,652 A | 12/1998 | Schildgen et al. | |
| 5,987,746 A | 11/1999 | Williams et al. | |
| 5,991,667 A | 11/1999 | Feith | |
| 6,253,110 B1 | 6/2001 | Brabec et al. | |
| 6,284,682 B1 | 9/2001 | Troczynski et al. | |
| 6,361,780 B1 | 3/2002 | Ley et al. | |
| 6,363,286 B1 | 3/2002 | Zhu et al. | |
| 6,426,114 B1 | 7/2002 | Troczynski et al. | |
| 6,709,514 B1 | 3/2004 | Hossainy | |
| 6,730,324 B2 | 5/2004 | Troczynski et al. | |
| 6,770,325 B2 | 8/2004 | Troczynski et al. | |
| 6,889,092 B2 | 5/2005 | Zhu et al. | |
| 6,896,965 B1 | 5/2005 | Hossainy | |
| 7,115,300 B1 | 10/2006 | Hossainy | |
| 7,174,221 B1 | 2/2007 | Chen et al. | |
| 7,247,364 B2 | 7/2007 | Hossainy et al. | |

(Continued)

FOREIGN PATENT DOCUMENTS

WO  WO-02/13785 A2  2/2002

(Continued)

OTHER PUBLICATIONS

"PCT Application No. PCT/US2007/007558, International Search Report mailed Sep. 20, 2007", 5 pgs.

(Continued)

*Primary Examiner*—George Manuel
*Assistant Examiner*—Shubatra Narayanaswamy
(74) *Attorney, Agent, or Firm*—Faegre & Benson LLP

(57) ABSTRACT

A cardiac lead comprising a lead body extending from a proximal end portion to a distal end portion; a cardiac electrode disposed along the lead body; and a coating associated with at least a portion of the electrode, the coating comprises a conductive polymer.

14 Claims, 2 Drawing Sheets

U.S. PATENT DOCUMENTS

| | | | |
|---|---|---|---|
| 7,279,175 | B2 | 10/2007 | Chen et al. |
| 2002/0022826 | A1* | 2/2002 | Reynolds et al. ......... 604/890.1 |
| 2002/0138123 | A1 | 9/2002 | Casas-Bejar et al. |
| 2003/0031699 | A1 | 2/2003 | Van Antwerp |
| 2003/0073961 | A1* | 4/2003 | Happ ......................... 604/274 |
| 2003/0093136 | A1 | 5/2003 | Osypka et al. |
| 2004/0037886 | A1 | 2/2004 | Hsu |
| 2004/0063805 | A1 | 4/2004 | Pacetti et al. |
| 2005/0070985 | A1 | 3/2005 | Knapp et al. |
| 2005/0080470 | A1 | 4/2005 | Westlund et al. |
| 2005/0180919 | A1 | 8/2005 | Tedeschi |
| 2006/0235499 | A1 | 10/2006 | Heil, Jr. et al. |
| 2007/0051531 | A1 | 3/2007 | Borgaonkar et al. |
| 2007/0128246 | A1 | 6/2007 | Hossainy et al. |
| 2007/0190104 | A1 | 8/2007 | Kamath et al. |
| 2008/0009939 | A1 | 1/2008 | Gueriguian et al. |
| 2008/0051866 | A1 | 2/2008 | Chen et al. |
| 2008/0167710 | A1 | 7/2008 | Dave et al. |
| 2009/0054961 | A1 | 2/2009 | Borgaonkar et al. |

FOREIGN PATENT DOCUMENTS

| | | |
|---|---|---|
| WO | WO-2005/035655 A1 | 4/2005 |
| WO | WO 2005035655 A1 * | 4/2005 |
| WO | WO-2007/030722 A1 | 3/2007 |
| WO | WO-2007/126806 A1 | 11/2007 |
| WO | WO 2009/051945 | 4/2008 |

OTHER PUBLICATIONS

"PCT Application No. PCT/US2007/007558, Written Opinion mailed Sep. 20, 2007", 7 pgs.

07754128.2, "European Application Serial No. 07754128.2, Office Action Mailed Feb. 19, 2009", 3 pages.

Response filed Aug. 31, 2009 to Office Action dated Feb. 19, 2009, EP App 07754128.

Office Action issued in EP 07754128 mailed Mar. 31, 2010.

International Preliminary Report on Patentability, Chapter II, issued in PCT/US2006/035064, dated Sep. 12, 2007, 12 pages.

International Search Report and Written Opinion issued in PCT/US2006/035064, filed Jan. 23, 2007.

Kirby, Darren, "Use of a Bioactive Material on a Pacemaker Electrode for the Purpose of Enhancing Heart Pace/Sense Efficiency", MSC Biomedical Engineering, Thesis, Thrinty College Dublin (2003).

York, P., "New Materials and Systems for Drug Delivery and Targeting", Chemical Aspects of Drug Delivery Systems, Copyright 1996, pp. 1-10, proceedings from a symposium held Apr. 17-18, 1996 at Salford University.

* cited by examiner

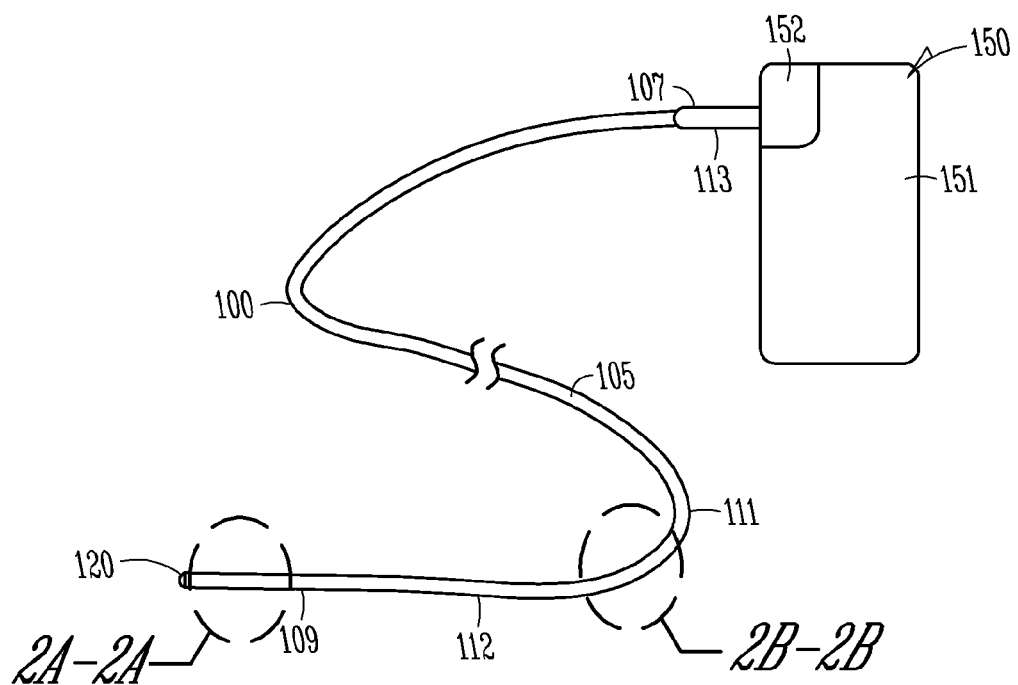
*Fig.1*
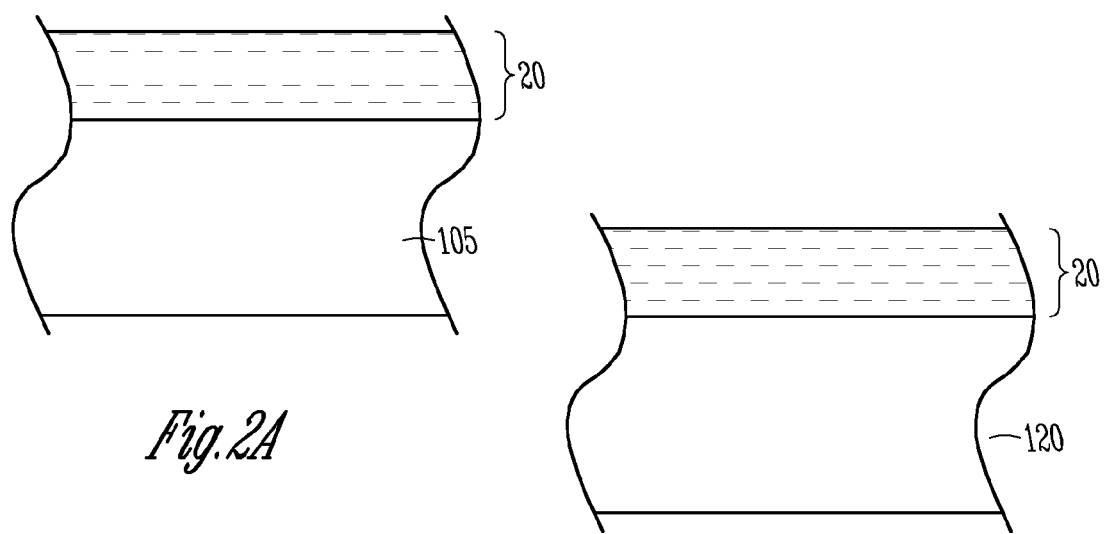
*Fig.2A*
*Fig.2B*

CONDUCTIVE POLYMERIC COATING WITH OPTIONAL BIOBENEFICIAL TOPCOAT FOR A MEDICAL LEAD

TECHNICAL FIELD

This invention relates to the field of medical leads, and more specifically to leads with conductive coatings.

BACKGROUND OF THE INVENTION

Leads having electrodes implanted in or about the heart have been used to reverse life-threatening arrhythmia or to stimulate contraction of the heart. For example, electrical energy is applied to the heart via an electrode to return the heart to normal rhythm. Leads are usually positioned on or in the ventricle or the atrium and the lead terminals are attached to a pacemaker or defibrillator which is implanted subcutaneously.

An issue concerning, for example, pacemaker leads is the increase in stimulation threshold, both acute and chronic, caused by the interaction between the electrode and body tissue at the point of implant. Approaches to reducing the threshold include silicone rubber based drug collars or plugs containing dexamethasone. However, in both cases, the lead design needs to accommodate the physical size of the plug or collar matrix. Also, dexamethasone is not very potent. Hence, high dosing is generally required. Moreover, these devices fail to address many of the physiological processes involved in the healing response upon lead implantation. Thus, there is a need for leads and/or electrodes that are constructed to more fully address the healing process so as to maintain optimal acute and chronic thresholds. In particular, there is a need for improved electrode performance.

SUMMARY OF THE INVENTION

One embodiment provides a cardiac lead comprising: a lead body extending from a proximal end portion to a distal end portion; a cardiac electrode disposed along the lead body; and a coating associated with at least a portion of the electrode, wherein the coating comprises a conductive polymer.

Another embodiment provides a cardiac lead comprising: a lead body extending from a proximal end portion to a distal end portion; a cardiac electrode disposed along the lead body; and a coating associated with at least a portion of the electrode, wherein the coating comprises sulfonated polytetrafluorethylene.

Another embodiment provides a cardiac lead comprising: a lead body extending from a proximal end portion to a distal end portion; a cardiac electrode disposed along the lead body; and a coating associated with at least a portion of the electrode, wherein the coating comprises poly(3,4-ethylenedioxythiophene)poly(styrenesulfonate).

Another embodiment provides a cardiac lead comprising: a lead body extending from a proximal end portion to a distal end portion; a cardiac electrode disposed along the lead body; and a coating associated with at least a portion of the electrode, wherein the coating comprises polypyrrole polystyrene sulfonate.

Another embodiment provides a method comprising covering a portion of a cardiac electrode with a coating, wherein the coating comprising at least one conductive matrix polymer layer comprising sulfonated polytetrafluorethylene, poly(3,4-ethylenedioxythiophene)poly(styrenesulfonate), polypyrrole polystyrene sulfonate, or a combination thereof; and delivering the medical electrode to a site of implantation.

Other embodiments provide methods to prevent fibrotic capsule formation or reduce chronic or acute threshold stimulation (when compared to a lead without a coating) by implanting a lead with a coating as described herein.

BRIEF DESCRIPTION OF THE DRAWINGS

FIG. 1 depicts a lead and pulse generator in accordance with at least one embodiment.

FIG. 2A depicts a portion of a lead with a coating in accordance with at least one embodiment.

FIG. 2B depicts a portion of an electrode with a coating in accordance with at least one embodiment.

DETAILED DESCRIPTION

Figure 3:
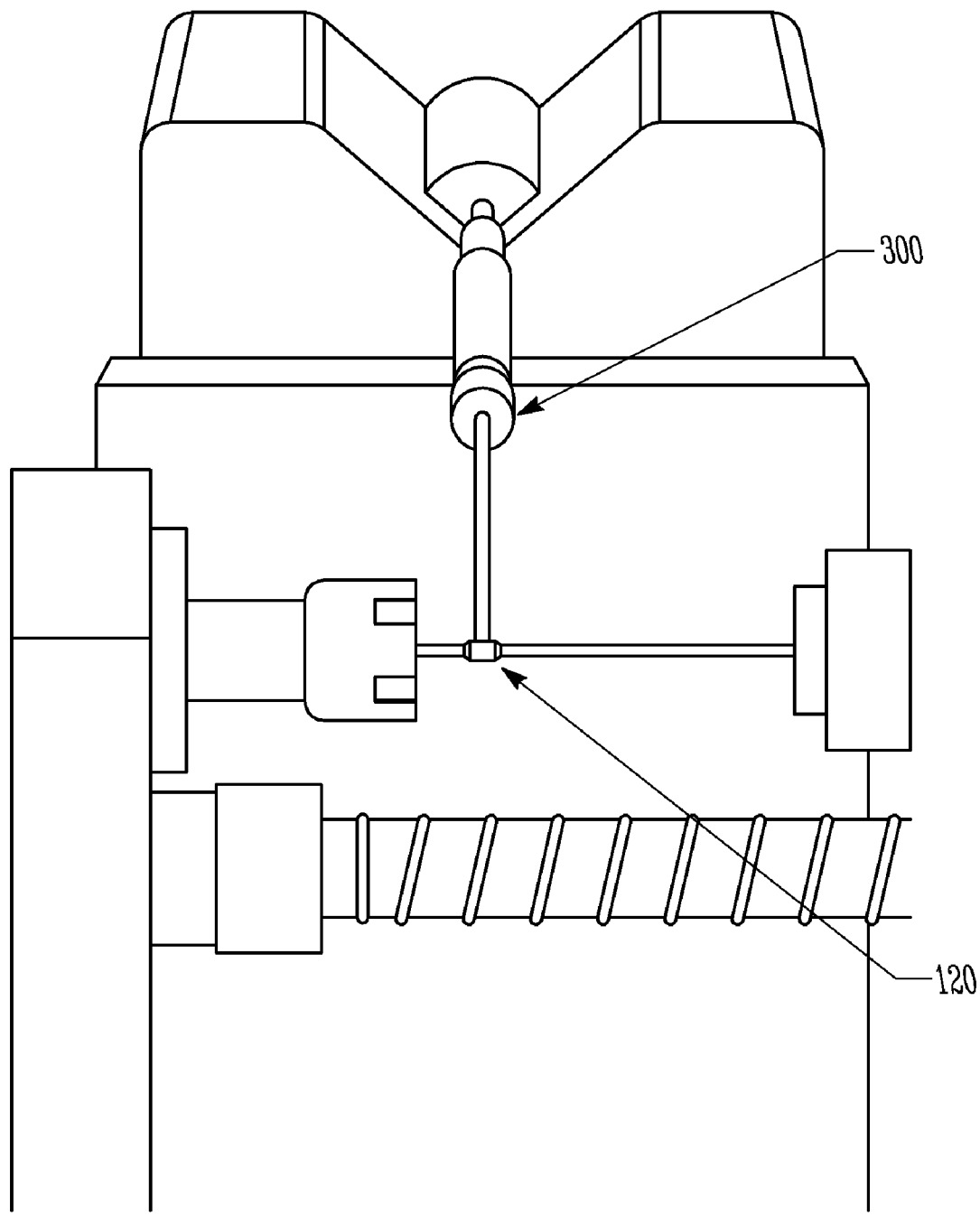
FIG. 3 depicts a device to apply a coating or agent to a lead or electrode in accordance with one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

The present device takes advantage of thin coatings of polymers and/or agents, such as therapeutic agents, applied to at least a portion of a lead and/or electrode. Thin coatings, when compared to plugs and collars, reduce the polymer burden as well as allow for even distribution of agents, including high potency therapeutic agents, and/or polymers on leads and/or electrodes. Additionally, thin coatings allow for the creation of leads with smaller diameters (no longer necessary to accommodate a plug or collar). Thus, one embodiment provides for the combination of agents with downsized implantable devices. The coatings may also provide reduced acute and/or chronic pacing thresholds and/or increased lead sensitivity. For example, a conductive polymer layer improves both impedance and biocompatibility.

The term "lead" is used herein in its broadest sense and includes any lead configuration available in the art, including, but not limited to, a stimulation lead, a sensing lead or a combination thereof. In one embodiment, the lead is adapted for active fixation. In another embodiment, the lead is adapted for passive fixation. In yet another embodiment, the lead is adapted for bipolar stimulation. In other embodiments, the lead is adapted for defibrillation and/or pacing/sensing. In one embodiment, the lead is tripolar or quadrupolar. In one embodiment, the lead comprises multiple electrodes.

For example, FIG. 1 shows a view of a lead 100 coupled to a pulse generator 150. In one embodiment, lead 100 is adapted to deliver pacing energy to a heart. Some examples deliver defibrillation shocks to a heart. Pulse generator 150 can be implanted in a surgically-formed pocket in a patient's chest or other desired location. Pulse generator 150 generally includes electronic components to perform signal analysis, processing and control. Pulse generator 150 can include a power supply such as a battery, a capacitor and other components housed in a case or can 151. The device can include microprocessors to provide processing and evaluation to determine and deliver electrical shocks and pulses of different energy levels and timing for ventricular defibrillation, cardioversion and pacing to a heart in response to cardiac arrhythmia including fibrillation, tachycardia and bradycardia.

In one embodiment, lead 100 includes a lead body 105 extending from a proximal end portion 107 to a distal end portion 109 and having an intermediate portion 111. Lead 100 includes one or more conductors, such as coiled conductors or other conductors, to conduct energy from pulse generator 150 to an electrode 120, and also to receive signals from the heart. The lead further includes outer insulation 112 to insulate the conductor. The conductors are coupled to one or more electrodes, such as electrode 120. Lead terminal pins 113 are attached to pulse generator 150 at a header 152. The system can include a unipolar system with the case acting as an electrode or a bipolar system with a pulse between two distally located electrodes. In some examples, pulse generator can 151 can be used as an electrode. In some examples, a header electrode can be placed in or near the header 152 of can 151.

Lead/Electrode Coatings

According to one embodiment, FIG. 2A depicts a coating 20 on a lead body 105; while according to another embodiment, FIG. 2B depicts a coating 20 on an electrode 120. Generally, a coating 20 may include at least one of: a primer layer, a matrix polymer layer, which may include one or more agents admixed therein, a topcoat layer (e.g., a bio-beneficial topcoat), which may include one or more agents admixed therein, and/or one or more agents on a lead 100 and/or electrode 120. The one or more agents can elute through or from a layer or can be provided without a layer (admixed or layered on top). In one embodiment, the polymer layer is a conductive polymer. In one embodiment, the polymer layer is porous. In another embodiment, the polymer layer is not porous.

The coating 20, which comprises one or more layers, is useful on any medical lead. For example, any medical implantable lead including, but not limited to, cardiac leads, including right-sided and left-sided cardiac leads, positive fixation leads where therapeutic agent is positioned at the fixation mechanism, positive fixation leads where therapeutic agent is positioned at the fixation mechanism that includes an electrode helix, epicardial leads that are sized for implantation through catheter delivery systems, downsized leads where coatings 20 are an option for positioning controlled release therapeutic agent delivery technology, neuro-stimulation leads requiring precise placement of electrode/therapeutic agent releasing components, miniaturized electrodes where coatings 20 can mask to produce high impedance and release agents, and miniaturized leads where a plurality of electrodes can be produced at specific locations by coating/masking.

The coatings also find use on implantable sensing devices, including, but not limited to ion sensors, potassium, $Ca^+$ and glucose.

A. Primer Layer

One embodiment provides a primer layer. The optional primer layer can be applied between the lead (e.g., between the outer insulation 112 and another layer) or electrode and another layer to improve the adhesion of the layer/coating 20 to the lead or electrode. The primer is applied to, for example, the surface of the lead and/or electrode prior to application of another layer, such as the matrix polymer layer, optionally admixed with one or more agents, the topcoat layer, optionally admixed with one or more agents and/or the agent(s). In one embodiment, the electrode surface is rough or a primer is applied prior to application of a polymer, such as a conductive polymer.

Primers include, but are not limited to, medical adhesives, acrylics and surface modification of the lead surface (e.g., silicone) with plasma, such as oxygen plasma (which modifies the surface of, for example, polymers (e.g., silicon), so that they can adhere more effectively with other materials, such as other layers within the coating 20 or adhesives).

B. Matrix Polymer Layer

Another embodiment provides a matrix polymer layer. Polymers for use in the matrix polymer layer include, but are not limited to, Solef® (Solef® 21508 polymer; PVDF copolymer ($VF_2$-HFP) from Solvay, Brussels, Belgium), Room-Temperature-Vulcanizing (RTV) silicone elastomers, silicone (any of a group of semi-inorganic polymers based on the structural unit $R_2SiO$, where R is an organic group), ethylene vinyl alcohol (E/VAL; a thermoplastic polymer), polyethylene (e.g., polyethylene glycol (PEG)), polycaprolactone, polylactide (PLA), polyglycolide (PGA), poly(lactide-co-glycolide) (PLGA) and/or polyurethane.

In one embodiment, the polymer layer includes a conductive material, such as a conductive polymer. Conductive polymers, also described as electroactive polymers, mainly comprise inherently conductive polymers and conductive plastics. The latter are traditional plastics, such as thermoplastics with the addition of conductive fillers, such as powdered metals or carbon (e.g., carbon black or fiber).

In one embodiment, the inherently conductive polymers (ICPs) contain conjugated electron backbones that display electronic properties. This results in a group of polymers that can be oxidized or reduced more easily and more reversibly than conventional polymers. Charge transfer agents (dopants) have an effect on this oxidation-reduction scenario and convert insulating polymers to conducting versions close to metallic conductivity in many instances.

In one embodiment, the electrons of the conductive polymers are free to move. For example, in one embodiment the polymer is made up of alternating single and double bonds along the backbone (e.g., conjugated). In another embodiment, a dopant species (e.g., a carrier allowing electrons to "hop" from one position to another along the polymer chain) is present.

In one embodiment, the conductive polymer has extended delocalized bonds (which may comprise aromatic units) that create a band structure similar to silicon. When charge carriers (from the addition or removal of electrons) are introduced into the conduction or valence bands the electrical conductivity increases.

Doping materials enhance the conductivity of a polymer and provide a lower energy threshold for conductivity. There are two primary methods of doping a conductive polymer, both through an oxidation-reduction (REDOX) process. The first method, chemical doping, involves exposing the polymer to an oxidant (e.g., iodine or bromine) or reductant (e.g., alkali metal). The second is electrochemical doping in which a polymer coated working electrode is suspended in an electrolyte solution in which the polymer is insoluble along with separate counter and reference electrodes. A potential difference is created between the electrodes which causes charge (and the appropriate counter ion from the electrolyte) to enter the polymer in the form of electron addition (n doping) or removal (p doping). Chemical n doping is preferably carried out in an environment of inert gas (e.g., argon). Doping materials can include, but are not limited to, iodine, bromine, lithium, sodium, polystyrene sulfonate (PSS) and salts of boron tetrafluoride. In one embodiment, electrically conductive coatings are deposited on the polymer surface or electrically conductive particles are blended with polymer. In one embodiment, the coating or particles comprise platinum, iridium, cobalt, silver, nickel, carbon (e.g., glassy carbon), stainless steel, titanium or combinations thereof.

Classes of conductive polymers include poly(acetylene)s, poly(pyrrole)s (PPy) (e.g., conductive polypyrrole polystyrene sulfonate), poly(thiophene)s (PT), poly(aniline)s, and poly(para-phenylene vinylene)s when combined with appropriate doping materials (e.g., doping materials are additives that facilitate the polymer conductivity). Conductive polymers also include silicone rubbers, polyurethane and homopolymers or copolymers of polyolefin, fluoropolymer, polyamide and polyester, combined with appropriate doping materials. Conductive polymers also include EHPT (poly(3-(2-ethylhexyl)thiophene), ionomers (e.g., Nafion®) and PEDOT (e.g., PSS/PEDOT).

1. Nafion®

Nafion® is a member of a class of synthetic polymers with ionic properties which are called ionomers. (Nafion® is available commercially in several forms from, for example, Aldrich, including, but not limited to, Nafion® NR50, Nafion® perfluorinated resin solution, Nafion® perfluorinated resin, aqueous dispersion, Nafion® perfluorinated resin, powder, Nafion® SAC-13, and Nafion®, trimethylsilylated.) Nafion® is a perfluorinated polymer that contains sulfonic (sulfonated polytetrafluoroethylene polymer or perfluorocarbonsulfonic acid) or carboxylic ionic functional groups (e.g., a sulfonated tetrafluorethylene copolymer or a carboxylated tetrafluorethylene copolymer (polytetrafluorethylene)). In one embodiment, the perfluorinated polymer contains sulfonic functional groups. In another embodiment, the perfluorinated polymer contains carboxylic ionic functional groups. In one embodiment, the structure of Nafion® ($C_7HF_{13}O_5S.C_2F_4$) is as follows:

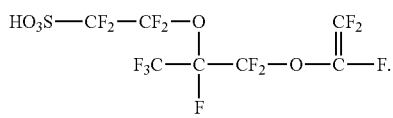

In another embodiment, the structure of Nafion® is as follows:

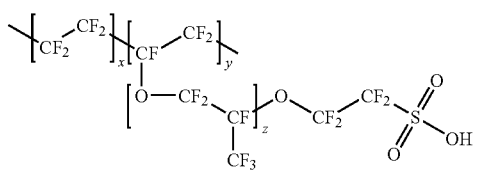

wherein x, y and z are each independently an integer (e.g., from about 1 to about 20 or greater).

2. PEDOT

PEDOT (also known as PEDT/PSS or PEDOT/PSS) is the commercial name for a mixture of two components. One component in this mixture is made up of sodium polystyrene sulfonate which is a sulfonated polystyrene in which part of the sulfonyl groups are deprotonated. The other component, poly(3,4-ethylenedioxythiophene), is a conjugated polymer based on polythiophene. The chemical name of PEDOT:PSS is poly(3,4-ethylenedioxythiophene)poly(styrenesulfonate).

In one embodiment, the conductive polymers are biocompatible (e.g., the polymers are not toxic or injurious to living tissue). Use of conductive polymers can reduce pacing threshold and improve sensing performance of the electrode along with improved biocompatibility of the electrode. For example, the use of conductive polymers on an electrode allows for the presentation of an organic interface to biological tissue instead of a metallic interface (e.g., a metallic electrode) for a favorable biological response to the implant. Inflammatory and healing response of the tissue can be controlled and altered to reduce myocyte necrosis in the area next to the lead and reduce thickness of fibrotic capsule (an optional topcoat layer may also be present.

C. Topcoat Layer

Another embodiment provides a topcoat layer. Topcoat layers, such as bio-beneficial polymer topcoats, can be formed from compounds including, but not limited to, phosphorylcholine (PC), polyvinylpyrrolidone (PVP), poly(vinyl alcohol) (PVA), hyaluronic acid (HA), and/or polyactive (a block copolymer composed of polyethylene oxide (PEO) and polybutylene terpthalate (PBT) or a copolymer of polyethylene glycol (PEG) and polybutylene terphalate). In one embodiment, topcoats are mixed with other components, such as the polymer matrix components discussed above. In another embodiment, the topcoat layer is applied on top of a polymer or agent layer.

Topcoat layers are beneficial especially when used on an electrode 120. By coating the electrode 120 with a topcoat layer, the patient's immune system is exposed to an inert polymer and not the metal electrode 120. It is believed that a phosphorycholine layer functions as an anti-macrophage adhesion surface, while a sodium hyaluronate (HA) layer functions as an anti-platelet adhesion surface.

In one embodiment, the topcoat layer is a proliferative, including but not limited to, hydroxyapatite (HAp). Hydroxyapatite (HAp) may promote the growth of excitable myocardial cells at the site of electrical stimulation (e.g., electrode 120). Reduced voltage and pulse width would be needed to stimulate the excitable myocardial cells (the stimulus would not have to overcome the non-excitable fibrotic barrier). Reduced stimulation voltage and pulse width would also reduce polarization at the lead tip, which would result in a lower stimulation impedance, and reduced likelihood of falsely sensing after-potential as cardiac activity. Reduced polarization at the lead electrode 120 would also improve electro-chemical corrosion and reduce pacemaker battery consumption. In one embodiment, the topcoat layer is not a proliferative.

In one embodiment, the topcoat layer on at least a portion of the electrode 120 is bio-degradable (e.g., bio-dissolvable). Bio-degradable topcoat layers can be formed from such polymers including but not limited to HA, PVA and/or PVP. In one embodiment, at least a portion of the lead 100 is coated with a bio-degradable topcoat layer. In another embodiment, at least a portion of the lead 100 is coated with a polymer that is not bio-degradable.

D. Agents

One embodiment provides a drug eluting lead 100 or electrode 120 which comprises at least one therapeutic agent. The therapeutic agent includes, but is not limited to an anti-inflammatory, anti-proliferative, anti-arrhythmic, anti-migratory, anti-neoplastic, antibiotic, anti-restenotic, anti-coagulation, anti-clotting (e.g., heparin, coumadin, aspirin), antithrombogenic or immunosuppressive agent, or an agent that promotes healing, such as a steroid (e.g., a glucocorticosteriod), and/or re-endothelialization or combinations thereof.

In essence, any drug or bioactive agent which can serve a useful therapeutic, prophylactic or even diagnostic function when released into a patient can be used. The agents may be used alone, in combinations of agents, admixed with a layer or applied on top of, underneath or between layers of the coating 20.

More specifically, the therapeutic agents may include, but are not limited to paclitaxel, clobetasol, rapamycin (sirolimus), everolimus, tacrolimus, actinomycin-D, dexamethasone (e.g., dexamethasone sodium phosphate or dexamethasone sodium acetate), mometasone furoate, vitamin E, mycophenolic acid, cyclosporins, beclomethasone (e.g., beclomethasone dipropionate anhydrous), their derivatives, analogs, salts or combinations thereof.

In one embodiment, a combination of an anti-proliferative (e.g., everolimus or paclitaxel) and an anti-inflammatory (e.g., dexamethasone, clobetasol or mometasone furoate) agent may be employed. In one embodiment, a combination of dexamethasone and everolimus is employed. In another embodiment, a combination of clobetasol and everolimus is employed. In yet another embodiment, a combination of dexamethasone and paclitaxel is employed. In another embodiment, a combination of clobetasol and paclitaxel is employed. In another embodiment, a combination of dexamethasone and sirolimus is employed. In one embodiment a combination of clobetasol and sirolimus is employed.

Additional suitable agents can be found in the Physicians Desk Reference (PDR) (see, for example, *The Physicians Desk Reference* (59th ed. 2005).

The therapeutic agent can be present in any effective amount. An "effective amount" generally means an amount which provides the desired local or systemic effect. For example, an effective dose is an amount sufficient to affect a beneficial or desired clinical result. The precise determination of what would be considered an effective dose may be based on factors individual to each patient, including their size and age. In one embodiment, the therapeutic agent is present in a concentration of less than about 100 μg/cm$^2$. For example, the agent may be present in a range of about 2 to about 10 μg/cm$^2$, about 10 to about 20 μg/cm$^2$, about 20 to about 30 μg/cm$^2$, about 30 to about 40 μg/cm$^2$, about 40 to about 50 μg/cm$^2$, about 50 to about 60 μg/cm$^2$, about 60 to about 70 μg/cm$^2$, about 70 to about 80 μg/cm$^2$, about 80 to about 90 μg/cm$^2$ and/or about 90 to about 100 μg/cm$^2$. The agent(s) may also be present at a concentration of higher than about 100 μg/cm$^2$.

In one embodiment, the agent eluting leads and/or electrodes can be delivered to a desired site within the patient's body. Once implanted, the therapeutic agent may elute from the surface of the implant and diffuse into the adjoining tissue. In this manner, the inflammatory process and/or other unwanted biological processes associated with implantation and the presence of the foreign object is suppressed (e.g., reduced inflammation and/or toxicity of inflammatory response). Additionally, the growth of non-excitable, connective tissue around the electrode (e.g., the capsule) is reduced (e.g., a reduction in fibrotic capsule thickness may be observed), and thus, the postoperative rise in the stimulation threshold lessens, a stable reduced threshold (when compared to the use of a lead without a coating 20 as described here), both acute and chronic, is thereby provided. Additionally, the device and methods may prevent myocyte cell function impairment and/or necrosis around, near or on an electrode 120, which may further stabilize a reduced threshold.

In one embodiment, the therapeutic agent is available immediately after and/or during implantation (time of injury). In another embodiment, within a few days, such as about 1 to about 5 days, following implantation, the agent has nearly completely eluted. In another embodiment, the therapeutic agent elutes in a couple of hours to several days to several weeks (e.g., in about 1 to about 5 weeks). The therapeutic agent may also be designed to have longer eluting times, such as several months. Additionally, the lead may be designed so that one therapeutic agent is released at the time of implantation (time of injury), while another therapeutic agent releases more slowly, for example, over the course of about several weeks to about a month or two from the time of implantation. In one embodiment, the therapeutic agents may be the same or different therapeutic agents.

Method of Manufacture

In one embodiment at least one agent, polymer and/or topcoat are admixed, for example, with a solvent to provide a solution or mixture. In one embodiment, the solvent does not interfere with the activity of the agent. Examples of such solvents include water, alcohol, cyclohexanone, acetone, acetonitrile and combinations thereof. The solution can be applied to at least a portion or all of a lead 100 and/or electrode 120 by, for example, spray coating. After the solvent in the solution is evaporated, a thin layer containing at least one agent, polymer and/or topcoat remains on the surface of the lead 100 and/or electrode 120. The process can be repeated as many times as desired. Alternatively, the coating 20 can be applied to the lead 100 and/or electrode 120 by dip-coating, brush-coating, drop coating or the coating can be electrode-posited. For example, a coating of Nafion® and/or PEDOT (e.g., PEDOT/PSS) from solution using appropriate solvent can be applied on an electrode surface using spray and/or drop coating methods followed by an optional top coat of one of the above mentioned biobeneficial polymers using spray and/or drop coating methods. RF magnetron physical vapor deposition sputtering process may also be employed. The coating 20 may also be applied using one or more of spraying, dipping, electrodeposition, electrochemical deposition, electrospinning, sputtering and/or brushing.

In one embodiment, a PEDOT compound is applied to an object of interest, such as a lead 100 or an electrode 120 of a lead, as a dispersion of gelled particles in water. For example, it can be spin-coated onto conductive and non-conductive substrates, including at least a portion of a lead body and/or electrode 120, and the water can be removed by the application of heat. A water solution of polystyrenesulfonate doped PEDOT can be obtained from BAYER AG Germany under the trade name BAYTRON® P. The Monomer is available as BAYTRON® M.

In one embodiment, conductive polymers, such as PPy and PEDOT, can be formed by passing a current through an electrode while the electrode is immersed in an aqueous solution of the monomer. This leads to the formation of a rough, foam-like coating that is held onto the electrode by electrostatic forces. The foam will trap other molecules that are present in the solution while it is forming (e.g., therapeutic agents or biomolecules (e.g., ligands or antibodies against cell surface proteins) promoting attachment to tissue (e.g., cardiac tissue)).

In one embodiment, a coating 20 comprising one or more layers ranges from about submicron to about 10 microns in thickness, about 1 to about 50 microns in thickness or about 50 to about 100 microns in thickness. In another embodiment, the thickness of the coating 20 ranges from about 1 to about 5, about 5 to about 10 microns, about 10 to about 15, about 15 to about 20, about 20 to about 30, about 30 to about 40, about 40 to about 50, about 50 to about 60, about 60 to about 70, about 70 to about 80, about 80 to about 90, or about 90 to about 100. In one embodiment, one or more layers are distributed evenly across a distal portion of a lead 100 and/or electrode 120. In another embodiment, one or more layers are distributed in a pattern across at least a portion of a lead 100 and/or electrode 120 surface (e.g., so as to have portions of, for example, the electrode uncovered (e.g., portions of the metal electrode are still exposed)). In one embodiment, one or more layers are applied to the lead body 100 adjacent to the electrode 120. In another embodiment, one or more layers are applied to the electrode 120.

FIG. 3 depicts a device that may be used to apply primer, polymer matrix layer, with or without one or more agents admixed therein, topcoat layer, with or without one or more agent admixed therein, and/or an agent to at least a portion of a lead and/or an electrode. A syringe, typically a motorized syringe 300 (filled with one or more agent, polymer or topcoat, or a mixture thereof in solution or as a mixture in a solvent) mounted on a syringe pump (e.g., a positive displacement pump that can accurately meter fluid, the advancement of which is controlled by a motor, such as a step motor) is connected to a hypodermic needle based nozzle assembly. The fluid dispensed from the needle can either be atomized to spray using pressured air on the nozzle or just droplets without using pressured air for coating at least a portion of a lead and/or electrode. The device can be rotated during this process so that all sides of the device are coated.

This process of spray coating allows for greater control of coating placement which thereby allows for accurate placement so as to selectively coat one area of the lead and/or electrode without contaminating other areas of the lead and/or electrode with the spray solution/mixture. Other benefits of the spray coating method are decreased waste of coating solution/mixture and uniform coating on the device (e.g., along a lead body or on an electrode). A uniform thickness and precise quantity will lead to uniform and consistent eluting of agent from the coated device surface.

Additionally, the coating of at least a portion of the lead 100 and/or the electrode 120 allows for therapeutic agent to be provided to the injured tissue from a large surface area. Furthermore, thin coatings and potent (chemically or medicinally effective) therapeutic agents provide for reduced polymer and therapeutic agent burden on the lead 100 and/or electrode 120, making it possible to reduce the lead 100 diameter. For example, therapeutic agents such as clobetasol and everolimus can be used at low doses, such as about 100 µg/cm$^2$ (much lower than that used for dexamethasone in lead collars and plugs) and be highly effective.

Any combination of layers (primer, matrix polymer layer, topcoat layer) and/or agents is envisioned; additionally the various components (primer, matrix polymer layer, topcoat layer, and/or agents) may be embedded within the lead. In one embodiment, the one or more layers and/or agent(s) are disposed on at least a portion of the lead 100 adjacent to the electrode 120. For example, in one embodiment, the agent(s) and/or layers(s) are applied directly to at least a portion of the lead 100 and/or electrode 120. In one embodiment, at least a portion of the lead 100 and/or electrode 120 is coated with a primer. In another embodiment, at least a portion of the lead 100 is coated with primer layer and/or a matrix polymer layer. In another embodiment, at least a portion of the lead 100 is coated with primer, matrix polymer layer and/or a topcoat layer. In another embodiment, at least a portion of the lead 100 is coated with matrix polymer layer. In another embodiment, at least a portion of the lead 100 is coated with a matrix polymer layer and/or a topcoat layer. In another embodiment, at least a portion of the lead 100 and/or electrode 120 are coated with topcoat layer and/or agent. In another embodiment, at least a portion of the lead 100 and/or electrode 120 are coated with an agent (e.g., a therapeutic agent or drug).

In one embodiment, one or more agents are applied directly onto at least a portion of the lead 100 and/or the electrode 120. In another embodiment, one or more agents are applied on top of a primer, matrix polymer layer and/or a topcoat layer. In another embodiment, one or more agents are admixed with the matrix polymer layer and/or the topcoat layer (e.g., prior to application of the layer). In another embodiment, one or more agents are applied between two or more layers of matrix polymer and/or two or more layers of topcoat. The agents admixed in the layers and/or applied on top of or between the layers can be the same or different. For example, in one embodiment, the agent admixed with the matrix polymer layer is different from the agent admixed in the topcoat layer.

One embodiment provides a matrix polymer layer applied alone to at least a portion of the lead 100, applied after a primer, applied after an agent, and/or admixed with one or more agents, and/or followed by another layer of matrix polymer and/or a topcoat layer or agent. Another embodiment provides a bio-beneficial topcoat over one or a mixture of anti-inflammatory and anti-proliferative agents, including dexamethasone, such as dexamethasone acetate, cloebasol and everolimus in a matrix polymer. Another embodiment provides a lead 100 comprising a bio-beneficial polymer topcoat over a drug eluting polymer matrix layer comprising clobetasol and/or everolimus in Solef®. Such a combination will give an anti-thrombogenic surface and will result in moderate and controlled acute inflammatory response.

In one embodiment, a topcoat is admixed with one or more agents or the agent is applied before or after the topcoat or in between two layers of topcoat. The topcoat can be applied directly to at least a portion of the lead 100 and/or electrode 120. A topcoat can also be applied to the matrix polymer layer, mixed with the matrix polymer layer, or on top of another topcoat layer.

In addition to the agent and/or layers (coating 20) being deposited on the surface of at least a portion of the electrode 120, the agent, polymer and/or topcoat may be deposited within interstices of a porous electrode (e.g., a porous platinum electrode) and/or other types of depressions (e.g., channels, grooves, bore holes) of the electrode. As a result of the addition of structure to the electrode, an increased amount of agent, primer, matrix polymer and/or topcoat may be deposited. The primer, matrix polymer, topcoat and/or agent may be applied into channels via an inkjet device or the syringe/needle apparatus depicted in FIG. 3 or any other method available.

In one embodiment, the agent, primer, matrix polymer and/or topcoat are applied to at least a portion of an electrode 120 which contacts tissue when implanted. In one embodiment, the coating 20 and/or agent(s) do not impede the function of the lead 100 and/or electrode 120 (e.g., the electrode 120 can pace through the coating 20 and/or agent(s)). In one embodiment, the coating 20 comprises an electrically conductive polymer. In one embodiment, the agent, primer, matrix polymer and/or topcoat are applied to at least a portion of a lead 100 and to at least a portion of an electrode 120.

One embodiment provides a layer of conductive polymer on at least a portion of an electrode with an optional layer of topcoat.

One embodiment provides a layer of polypyrrole (PPy; e.g., PPy doped with PSS), Nafion® or PEDOT (e.g., PEDOT/PSS) on at least a portion of an electrode 120 (e.g., pacing electrode). Another embodiment further provides a biobeneficial topcoat layer, such as HA, on top of the layer of polypyrrole (PPy; e.g., PPy doped with PSS), Nafion® or PEDOT (e.g., PEDOT/PSS).

Another embodiment provides a layer of PPy:PSS/HA and/or Nafion®/HA on at least a portion of an electrode (optionally admixed with a therapeutic agent), optionally followed by a layer of a therapeutic agent, followed by a second layer of PPy:PSS/HA and/or Nafion®/HA (optionally admixed with a therapeutic agent).

Another embodiment provides a layer of PPy:PSS or Nafion® on at least a portion of an electrode, followed by a HA topcoat, wherein the topcoat is optionally admixed or layered with a therapeutic agent.

One embodiment provides a layer of HA admixed with a therapeutic agent and PPy:PSS or Nafion® on at least a portion of an electrode.

Additionally, the primer, matrix polymer, topcoat and/or agent can be combined, cast into films and mounted on a lead 100 as a drug collar or formed into a polymer plug. For example, an electrode, such as an electrode tip (e.g., a cathode comprised of crenulated dome having a surface of polished platinum, platinum black, platinum/iridium, iridium oxide, titanium nitride, or other suitable electrode material), can be formulated so as to comprise a polymer plug of, for example, one or more agents and at least one polymer or topcoat. In one embodiment, the agents comprise a steroid and everolimus. In another embodiment, the therapeutic agent comprises everolimus. In one embodiment, the agent and polymer are admixed; in another embodiment, they are layered. The plug can be pre-made and inserted in the electrode or can be deposited in the space using syringe technology.

In one embodiment, dexamethasone (e.g., DSP or DA) and an anti-proliferative agent, such as everolimus, are delivered through a silicone collar and/or plug. In another embodiment, sodium hyaluronate (HA) is used as a drug delivery vehicle for anti-inflammatory and/or anti-proliferative agents in a plug and/or collar. In one embodiment, at least a portion of a lead helix, lead and/or electrode is coated with a mixture of HA and PC or a layer of PC followed by a layer of HA. Another embodiment provides a plug comprising a mixture of HA/PC/everolimus/DA. Another embodiment provides a collar comprising a mixture of HA/PC/everolimus/DA coated with layers of HA and PC.

All publications, patents and patent applications are incorporated herein by reference. It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac lead comprising:
a lead body extending from a proximal end portion to a distal end portion;
a cardiac electrode disposed along the lead body; and
a coating in contact with at least a portion of the electrode, the coating including a matrix polymer layer and a topcoat layer over the matrix layer,
where in the matrix polymer layer comprises at least one of sulfonated polytetrafluorethylene, poly(3,4-ethylenedioxythiophene) poly(styrenesulfonate) or polypyrrole polystyrene sulfonate and the topcoat layer comprises phosphorylcholine (PC), polyvinylpyrrolidone (PVP), poly(vinyl alcohol) (PVA), hyaluronic acid (HA), polyactive or a combination thereof.

2. The lead of claim 1, wherein the coating comprises sulfonated polytetrafluorethylene.

3. The lead of claim 1, wherein the coating comprises poly (3,4-ethylenedioxythiophene) poly(styrenesulfonate).

4. The lead of claim 1, wherein the coating comprises polypyrrole polystyrene sulfonate.

5. The lead of claim 1, further comprising at least one therapeutic agent.

6. The lead of claim 5, wherein the therapeutic agent is mixed in the coating.

7. The lead of claim 5, wherein the therapeutic agent is on top of or under the coating.

8. The lead of claim 5, wherein the therapeutic agent comprises an anti-inflammatory agent, anti-proliferative agent, anti-arrhythmic agent, anti-migratory agent, anti-neoplastic agent, antibiotic agent, anti-restenotic agent, anti-coagulation agent, anti-clotting agent, anti-thrombogenic agent, immunosuppressive agent, steroid or a combination thereof.

9. The lead of claim 5, wherein the therapeutic agent comprises paclitaxel, clobetasol, rapamycin, everolimus, tacrolimus, actinomycin-D, dexamethasone, vitamin E, mycophenolic acid, cyclosporin, beclomethasone or a combination thereof.

10. A method comprising:
covering a portion of a cardiac electrode with a coating, wherein the coating comprises a matrix polymer layer and a topcoat layer over the matrix layer,
wherein the matrix polymer layer comprises at least one conductive matrix polymer comprising sulfonated polytetrafluorethylene, poly(3,4-ethylenedioxythiophene) poly(styrenesulfonate), polypyrrole polystyrene sulfonate, or a combination thereof and the topcoat layer comprises phosphorylcholine (PC), polyvinylpyrrolidone (PVP), poly(vinyl alcohol) (PVA), hyaluronic acid (HA), polyactive or a combination thereof; and
delivering the cardiac electrode to a site of implantation.

11. The method of claim 10, further comprising contacting the matrix polymer layer with a therapeutic agent.

12. The method of claim 10, further comprising contacting the topcoat layer with a therapeutic agent.

13. The method of claim 10, wherein the coating is applied to a thickness of about 25 to about 100 microns.

14. The method of claim 10, wherein the coating is applied by spraying, dipping, drop coating, sputtering, brushing or a combination thereof.

* * * * *